United States Patent [19]

Twardzik et al.

[11] Patent Number: 5,248,666
[45] Date of Patent: * Sep. 28, 1993

[54] METHODS FOR INHIBITING NEOPLASTIC CELL PROLIFERATION USING PLATELET FACTOR 4

[75] Inventors: Daniel R. Twardzik, Bainbridge Island; George J. Todaro, Seattle, both of Wash.

[73] Assignee: Oncogen, Seattle, Wash.

[*] Notice: The portion of the term of this patent subsequent to May 20, 2003 has been disclaimed.

[21] Appl. No.: 877,341

[22] Filed: Apr. 29, 1992

Related U.S. Application Data

[60] Continuation of Ser. No. 159,935, Feb. 24, 1988, abandoned, which is a continuation-in-part of Ser. No. 115,139, Oct. 30, 1987, abandoned, which is a continuation-in-part of Ser. No. 20,609, Mar. 2, 1987, abandoned, which is a continuation-in-part of Ser. No. 912,407, Sep. 26, 1986, Pat. No. 4,737,580, which is a division of Ser. No. 712,302, Mar. 15, 1985, Pat. No. 4,645,828, which is a continuation-in-part of Ser. No. 592,969, Mar. 23, 1984, Pat. No. 4,590,003.

[51] Int. Cl.$^5$ .............................................. A61K 37/02
[52] U.S. Cl. .............................. 514/12; 514/2; 424/85.1; 530/324
[58] Field of Search ................ 514/2, 12; 530/324; 424/85.1

[56] References Cited

U.S. PATENT DOCUMENTS

| | | | |
|---|---|---|---|
| 4,529,594 | 7/1985 | Hayashi et al. | 514/12 |
| 4,530,901 | 7/1985 | Weissman . | |
| 4,543,329 | 9/1985 | Daum et al. . | |
| 4,565,785 | 1/1986 | Gilbert et al. . | |
| 4,582,800 | 4/1986 | Crowl . | |
| 4,590,003 | 5/1986 | Twardzik | 530/330 |
| 5,147,854 | 9/1992 | Newman et al. | 514/12 |

FOREIGN PATENT DOCUMENTS

| | | |
|---|---|---|
| 0133123 | 7/1984 | European Pat. Off. . |
| 0195087 | 9/1985 | European Pat. Off. . |
| 0196864 | 3/1986 | European Pat. Off. . |
| 84/03103 | 8/1984 | PCT Int'l Appl. . |
| 85/04397 | 10/1985 | PCT Int'l Appl. . |

OTHER PUBLICATIONS

Monoclonal Antibody Targeting of Anti-Cancer Agents in "New Experimental Modalities in the Control of Neoplasia" Ed. by Chandra.
"Suramin Inhibits Human Osteosarcoma Xenografts in Nude Mice" Cancer Research Walz et al. 51 3585–3589, Jul. 1991.
M. Poncs, et al., Cloning & Characterization of Platelet Factor 4 cDNA derived from a Human Erythroleukemic Cell Line, Chemical Abstracts, 106(1987) p. 165.
F. J. Morgan, et al, Complete Covalent Structure of Human Platelet Factor 4, Thrombos Haemostas (Stuttg.) (1979) 42:1652–1660.
Chemical Abstracts, 87 (1977) p. 183.
L. L. Brindley et al, Stimulation of histamine release from human basophils by human platelet factor 4, (1983) 72:1218–1223.
H. G. Klingeman et al, Beta-Thromboglobulin and HA-platelet factor 4 in multiple myeloma, Hodgkin disease and malignant lymphoma-effects of therapy, Thromb. Haemostasis, (1981) 46:1: p. 430, abstract no. 1380.

(List continued on next page.)

Primary Examiner—Nina Ossanna
Attorney, Agent, or Firm—Pennie & Edmonds

[57] ABSTRACT

Novel polypeptide compositions are provided which inhibit human tumor cell growth, which may or may not stimulate autophosphorylation of pp6src and induce the release of a 52 kD polypeptide from neoplastic cells. Individual polypeptides may be isolated from mammalian blood platelets by selected extraction and purification procedures, may be synthesized or produced by hybrid DNA technology.

2 Claims, 3 Drawing Sheets

OTHER PUBLICATIONS

V. Miggiano et al, Murine monoclonal antibodies against human beta-thromboglobulin (betaTG), *Chemical Abstracts*, (1982) 96:ref. no. 102116s.

J. W. Lawler, "Prediction of the secondary structure of platelet factor 4 and beta-thromboglobuoin from their amino acid sequences", *Thrombosis Research*, (1981) 21:121-127.

D. Paul et al., "Platelet basic protein: A mitogenic peptide for 3T3 cells secreted by human platelets", *Chemical Abstracts*, (1980) 93:11, p. 130 ref. no 107692z.

J. Folkman, "Angiogenesis: Initiation and modulation", *Symp. Fund. Cancer Res.*, (1983) 36:201-208.

J. Folkman, "The role of heparin in angiogenesis", *CIBA Found. Symp.* (1983) 42:1652-1660.

M. Hermodson, et al., Isolation, Crystallization, and Primary Amino Acid Sequence of Human Platelet Factor 4, *J. Biol. Chem*, (1977) 252:6276-6279.

S. Taylor & J. Folkman, Protamine is an Inhibitor of Angiogenesis, *Nature* (1982) 297:307-312.

Chemical Abstracts, 103 (1985) p. 616.

```
                                        860          870          880          890
                                         ::           ::           ::           ::
                              CGC GCC ATG GAA GCT GAA GAG GAT GGA GAT CTG CAA
                              Arg Ala Met Glu Ala Glu Glu Asp Gly Asp Leu Gln
                                BssHII
            900          910      920          930          940          950
             ::           ::       ::           ::           ::           ::
TGC CTG TGC GTT AAG ACT ACG TCT CAG GTT AGA CCG CGG CAT ATC ACT AGC CTC GAG
Cys Leu Cys Val Lys Thr Thr Ser Gln Val Arg Pro Arg His Ile Thr Ser Leu Glu 960          970          980          990         1000
             ::           ::           ::           ::           ::
GTT ATC AAA GCG GGC CCA CAC TGT CCG ACT GCG CAG CTG ATC GCG ACT CTG AAA AAC
Val Ile Lys Ala Gly Pro His Cys Pro Thr Ala Gln Leu Ile Ala Thr Leu Lys Asn 1010         1020         1030         1040         1050         1060
  ::           ::           ::           ::           ::           ::
GGC CGT AAA ATA TGT CTG GAT CTG CAG GCA CCG CTG TAC AAG AAA ATC ATC AAA AAG
Gly Arg Lys Ile Cys Leu Asp Leu Gln Ala Pro Leu Tyr Lys Lys Ile Ile Lys Lys

1070         Bam HI
               ::
CTT CTC GAG TCT TGA GGATCCGTC...
Leu Leu Glu Ser ---
```

FIG. 3

METHODS FOR INHIBITING NEOPLASTIC CELL PROLIFERATION USING PLATELET FACTOR 4

CROSS-REFERENCE TO RELATED APPLICATIONS

This is a continuation-in-part, of application Ser. No. 07/159,935, filed Feb. 24, 1988, now abandoned, which is a continuation-in-part of application Ser. No. 115,139, filed Oct. 30, 1987, now abandoned, and application Ser. No. 020,609, filed Mar. 2, 1987, now abandoned, the latter being a continuation-in-part of application Ser. No. 912,407, filed Sept. 26, 1986, now U.S. Pat. No. 4,737,580, which is a divisional of application Ser. No. 712,302, filed Mar. 15, 1985, now U.S. Pat. No. 4,645,828, issued Feb. 24, 1987, which is a continuation-in-part of application Ser. No. 592,969, filed Mar. 23, 1984, now U.S. Pat. No. 4,590,003, issued May 20, 1986, which applications are incorporated herein by reference.

TECHNICAL FIELD

Cell growth regulatory compositions are disclosed, where the compounds preferentially inhibit growth of neoplastic cells.

BACKGROUND

The complexity of the regulation of differentiation and proliferation of and by hematopoietic cells is becoming increasingly apparent as the list of factors which are isolated which control these events continuously increases. For the most part, these factors are present in extraordinarily minute amounts in conjunction with numerous other proteins which serve a wide variety of functions. Factors which have been isolated and demonstrated to have activity include polypeptides and proteins such as Y-interferon, platelet-derived growth factor, colony stimulating factor, interleukin-2, erythropoietin, as well as numerous other lymphokines. There is substantial interest in the isolation, purification and characterization of these blood components as well as efficient preparation of large amounts of these peptides because of their possible use in cancer treatment, as well as their use in studying diseases such as cancer.

RELEVANT LITERATURE

Holley et al., *Proc. Natl. Acad. Sci. USA* (1980) 77:5989-5992, describe the purification of epithelial cell growth inhibitors. Nelsen-Hamilton and Holley, ibid. (1983) 80:5636-5640, describe the effect of a growth inhibitor and epidermal growth factor in the incorporation of radiotagged methionine into proteins secreted by African green monkey cells (BSC-1). Morgan et al., *Thromb. Haemost.* (1980) 42:1652-60 provide the amino acid sequence for human platelet factor 4. Dawes et al., *Thromb. Res.* (1983) 29:569-81 and Schernthaner et al., *Acta Med. Austriaca* (suppl.) (1979) 6:375-9 report polyclonal antibodies to platelet factor 4. Lawler, *Thromb. Res.* (1981) 21:121-7 Compares the sequences and structures of β-thromboglobulin and platelet factor 4. Taylor et al., *Nature* (1982) 297:307-312 disclosed that platelet factor 4 produces an avascular zone on the chick chorioallantoic membrane and that angiogenesis inhibitors may possibly be used clinically to treat highly angiogenic neoplasms such as brain tumors. However protamine, another angiogenesis inhibitor, was shown to have no direct cytotoxicity towards cultured tumor cells and in some instances even stimulated growth. Machin et al., *J. Mol. Biol.* (1984) 172:221-222 disclosed crystallization of platelet factor 4. Folkman et al. in Ciba Symposium 100 (1983) p. 132-139 (Pitman Books, London) disclosed that platelet factor 4 inhibits heparin-promoted angiogenesis.

SUMMARY OF THE INVENTION

Polypeptide compositions, and methods for their use, are provided which are characterized by having at least one of the following properties: capable of inhibiting tumor growth, while not inhibiting normal cell growth; capable of stimulating pp60src autophosphorylation; capable of inducing secretion of a 52 kD protein from tumor cells; and having a substantially equivalent amino acid sequence to at least a portion of a polypeptide isolatable from mammalian platelets and exhibiting at least one of the previously-indicated properties. Methods of preparation include cloning and expression in prokaryotic cells.

DESCRIPTION OF THE SPECIFIC EMBODIMENTS

Compositions comprising polypeptides, derivatives, fragments, or analogs thereof and formulations containing such compositions are provided which inhibit mammalian neoplastic cell growth. The subject polypeptides are related to a naturally occurring polypeptide called platelet factor 4 present in the ethanolic HCl fraction obtained by extraction of platelets.

Human platelet factor 4 has the following sequence: E-A-E-E-D-G-D-L-Q-C-L-C-V-K-T-T-S-Q-V-R-P-R-H-I-T-S-L-E-V-I-K-A-G-P-H-C-P-T-A-Q-L-I-A-T-L-K-N-G-R-K-I-C-L-D-L-Q-A-P-L-Y-K-K-I-I-K-K-L-L-E-S The polypeptides are stable at moderate temperatures (0°-250° C.), at a low pH, generally below about pH 3, usually at pH 2. The polypeptides have a molecular weight in the range of about 5,000-8,000, more exactly in the range of about 6,000-7,500, more particularly about 7,000. Platelet factor 4 is obtained from platelets of higher mammals, particularly primates, more particularly humans.

The polypeptide compounds which are employed will have from about 15 to 80 amino acids, where the naturally occurring polypeptides and mimetic analogs thereof will have from about 60 to 75 amino acids, more usually from about 65 to 72 amino acids, while fragments will generally range from about 15 to 60 amino acids, more usually from about 15 to 35 amino acids. Of particular interest are polypeptides having from about 58 to 72 amino acids, more particularly 69, 70 or 71 amino acids. These polypeptides may be joined to other compounds, such as antigens, receptors, labels, or the like.

Platelet factor 4-like materials, including platelet factor 4 fragments, mutants of the polypeptide, as well as fusion peptides comprising platelet factor 4 or a functional portion thereof, having the biological activity of the intact platelet factor 4 including cell growth modulation activity, receptor binding activity, and immunologic activity are also provided.

The polypeptides of this invention include congeners of platelet factor 4, namely compounds having at least one biological activity corresponding to that of platelet factor 4 and having at least one amino acid sequence having substantially the same amino acid sequence as platelet factor 4, where the congener may be of greater or lesser amino acid number than platelet factor 4. Biological activity includes immunological cross-reactivity with naturally-occurring platelet factor 4, or binding to a platelet factor 4 receptor molecule with high affinity. By "immunological cross-reactivity" is meant that an antibody induced by a novel polypeptide of this invention will cross-react with intact platelet factor 4, at least when platelet factor 4 is in a denatured state. By "high affinity" is meant a dissociation constant (Kd) of at least about $10^{-7}$M. By "platelet factor 4 receptor" is meant a binding site on the surface of a cell which specifically binds platelet factor 4 with high affinity, the binding being saturable and not inhibited by structurally unrelated polypeptides. Some of the polypeptides may also retain the cell growth modulatory activity of naturally occurring platelet factor 4, which includes inhibition of growth of neoplastic cells. The cell growth modulatory activity may be different from naturally occurring platelet factor 4, usually reduced. The polypeptides will have at least one biologically active sequence, e.g., immunological or epitopic, and may have more than one biologically active sequence, where such sequence can compete with a naturally occurring product for the biological property.

The definitions of the amino acids are set forth below.

| Neutral (Ne) | |
|---|---|
| aliphatic (Al) | |
| unsubstituted | G, A, V, L, I, P |
| substituted | |
| oxy | S, T |
| thio | C, M |
| amido | N, Q |
| aromatic (Ar) | |
| unsubstituted | F |
| substituted | Y |
| heterocyclic | H, W |
| Charged (at pH 6.0) | |
| basic | K, R |
| acidic | D, E |

The abbreviations in parentheses refer to the particular amino acid groups. By unsubstituted is intended no other heterosubstituents than the carboxy and amino group present in glycine. The amino acids are the naturally occurring L-amino acids.

The neutral amino acids may also be described as having non-polar or polar (but uncharged) R groups. The amino acids which come within these definitions are as follows:

| Non-polar amino acids | A, V, L, I, P, M, F, W |
|---|---|
| Polar amino acids | G, S, T, C, Y, N, Q |

Compositions of interest will have an acidic (anionic) N-terminus and a basic (cationic) C-terminus, where the charged regions will be from 6 to 15 amino acids, usually 6 to 12 amino acids, where the region will include an amino acid sequence of from 6 to 8 amino acids where at least 50%, usually 60% are ionic amino acids and usually not more than 90% are ionic amino acids.

Those compositions having at least about 60 amino acids will have the charged domains separated by at least 25 amino acids, usually at least 40 amino acids and fewer than about 70, usually fewer than about 65 amino acids. The amino acid linking sequence separating the charged domains will usually have an excess of cationic over anionic amino acids, generally having from about a 1.5 to 3, usually about 2 to 1 ratio, with the pK of the compound in the range of about 6.5 to 8, particularly about 7.4.

There will usually be two disulfide bridges in the linking sequence, where the bridging disulfides are from about 20 to 45, usually 22 to 40 amino acids apart, preferably separated by about 25 to 39 amino acids. The cysteines proximal to the N-terminus will be from about 8 to 16 amino acids from the N-terminus, with the cysteines proximal to the C-terminus about 12 to 45 amino acids, usually about 16 to 40 amino acids, from the C-terminus.

Compositions of interest will usually have a sequence proximal to the N-terminus, which has the formula of the pentapeptide E-A-E-E-D, more usually the decapeptide E-A-E-E-D-G-D-L-Q-C, frequently the pentadecapeptide E-A-E-E-D-G-D-L-Q-C-L-C-V-K-T, and more frequently having the following formula:

E-A-E-E-D-C-D-L-Q-C-L-C-V-K-T-T-S-Q-V-R-P-R-H where the letters have the following meaning in accordance with convention:
A - alanine
C - cysteine
D - aspartic acid
E - glutamic acid
G - glycine
H - histidine
L - leucine
P - proline
Q - glutamine
R - arginine
S - serine
T - threonine
V - valine It should be understood that conservative substitutions of amino acids may be made. Conservative changes include substitutions involving D and E; F and Y; K and R; G and A; N and Q; V, I and R, and the like. In some instances, non-conservative exchanges will be desirable, for example, substituting K or R with N or Q. This substitution is of particular interest where a dibasic amino acid protease cleavage site is present, e.g., K-R, where the substitution protects the site against proteolytic cleavage.

Also, insertions or deletions may be involved, where usually insertions or deletions will involve from 1 to 2 amino acids, particularly 1 amino acid.

Novel polypeptides of interest will for the most part have the following formula:

$Ac_R-M_R-Ba_R$ wherein:

$Ac_R$ (acidic region) is the N-terminal region and is characterized by having from 10 to 20 amino acids of which from four to five are acidic, at least two of the first three amino acids are acidic, two acidic amino acids are in tandem and a different two acidic amino acids are separated by a neutral aliphatic amino acid; two C residues are present separated by a single neutral aliphatic amino acid; the C-X-C is separated from D or E-X-D or E by from two to six amino acids;

$M_R$ is the middle region, either being a short linking group of from 2 to 30 carbon atoms, or having from about 25 to 40 amino acids; having two C residues separated from the cysteines of $Ac_R$ by at least 10, usually at least 20, amino acids and each of these C residues forming a disulfide bridge with one of the C residues in $Ac_R$; having from five to seven basic amino acids and from two to five, usually three to four, acidic amino acids;

$Ba_R$ (basic region) is the C-terminal region and is characterized by having from 12 to 30 amino acids; having two pairs of basic amino acids each succeeded by from two to three neutral aliphatic amino acids, either polar or non-polar, usually non-polar; having a P residue from 10 to 15 amino acids from the C-terminal amino acid.

Desirably $Ac_R$ will have the following formula (where two amino acids are indicated at the same site, either amino acid may be present at that site):

$$(H)—aa^1—aa^2—aa^3—\genfrac{}{}{0pt}{}{D}{E}—X^1—\genfrac{}{}{0pt}{}{D}{E}—aa^6—\genfrac{}{}{0pt}{}{D}{E}—aa^8—aa^9—X^2—C—aa^{11}—C—aa^{13}—\genfrac{}{}{0pt}{}{K}{R}—X^3$$

wherein:

(H) intends hydrogen at the N-terminus; $aa^{1,3}$ may be a bond or an aliphatic amino acid of from 2 to 6 carbon atoms, usually an acidic amino acid or a nonpolar amino acid of from 2 to 3 carbon atoms;

$aa^{1,3}$ may be a bond or an aliphatic amino acid of from 2 to 6 carbon atoms, usually an acidic amino acid or a non-polar amino acid of from 2 to 3 carbon atoms;

$aa^2$ may be a bond or an aliphatic amino acid of from 2 to 6 carbon atoms, usually a basic amino acid, polar amino acid of from 3 to 5 carbon atoms, or a non-polar amino acid of from 2 to 3 carbon atoms;

$x^1$ is a bond or amino acid sequence of from 1 to 2 amino acids of from 2 to 6, usually 4 to 6 carbon atoms, which are aliphatic non-polar or polar amino acids;

a is 0 or 1;

$aa^6$ is an aliphatic amino acid of from 2 to 6, usually 2 to 4 carbon atoms which may be non-polar or polar, or an acidic amino acid;

$aa^8$ is an aliphatic amino acid of from 2 to 6, usually 5 to 6 carbon atoms, usually non-polar;

$aa^9$ is an aliphatic amino acid of from 2 to 6, usually 4 to 6 carbon atoms, particularly polar carboxamide substituted or basic;

$x^2$ is a bond or an amino acid sequence of from 1 to 2 aliphatic amino acids of from 2 to 6 carbon atoms particularly neutral amino acids;

$aa^{11}$ is an aliphatic amino acid of from 2 to 6, usually 3 to 6 carbon atoms, which may be non-polar or polar;

$aa^{13}$ is an aliphatic amino acid of from 2 to 6, usually 5 to 6 amino acids, particularly non-polar;

$X^3$ is a bond, an hydroxyl, alkoxyl group of from 1 to 3 carbon atoms, amino, or an amino acid sequence of from 1 to 6, usually 1 to 3 amino acids, usually neutral aliphatic and either non-polar or polar, particuilarly polar, the fir5t three amino acids normally being neutral, wherein $X^3$ may terminate the molecule or be a link to $M_R$, $Ba_R$ or an antigen.

Preferred amino acids for the symbols are as follows:

$aa,^{1,3}$—bond, D, E, G, A;

$aa^2$—bond, G, A, K, R, S, T;

$x^1$—bond, (S or T)$_a$—(V, L or I)$_a$;

$aa^6$—S, T, G, A, D, E;

$aa^8$—V, L, I;

$aa^9$—N, Q, K, R;

$X^2$—(G or A)$_a$—(D or E)$_a$—(V, L or I)$_a$;

$aa^{11}$—V, L, I, M, S, T;

$aa^{13}$—V, L, I;

$X^3$—bond—(S or T)$_b$—(G, A, N or Q)$_a$—(V, I, or L)$_a$—(K, R, N, Q, H F or Y)$_a$;

a is 0 or 1; and b is an integer of from 0 to 3.

Desirably $Ba_R$ will have the following formula:

$$aa^{40}—aa^{41}—aa^{42}—\genfrac{}{}{0pt}{}{G}{A}—\genfrac{}{}{0pt}{}{S}{T}—aa^{45}—\genfrac{}{}{0pt}{}{K}{R}—aa^{47}—\genfrac{}{}{0pt}{}{G}{A}—\genfrac{}{}{0pt}{}{K}{R}—\genfrac{}{}{0pt}{}{K}{R}—$$

$$aa^{51}—C—aa^{53}—\genfrac{}{}{0pt}{}{D}{E}—aa^{55}—aa^{56}—aa^{57}—P—aa^{59}—aa^{60}—$$

$$\genfrac{}{}{0pt}{}{K}{R}—\genfrac{}{}{0pt}{}{K}{R}—aa^{63}—aa^{64}—aa^{64a}—\genfrac{}{}{0pt}{}{K}{R}—\genfrac{}{}{0pt}{}{K}{R}—aa^{67}—aa^{68}—X^4$$

where in:

$aa^{40,56}$ are an aliphatic acidic amino acid or amide thereof of from 4 to 5 carbon atoms;

$aa^{41,42,51,53,63,64,67}$ are aliphatic amino acids, particularly non-polar, of from 2 to 6, more particularly of from 5 to 6 carbon atoms;

$aa^{45}$ is an aliphatic amino acid of from 2 to 6 carbon atoms, particularly non-polar of from 4 to 6 carbon atoms, or a basic amino acid;

$aa^{47}$ is an aliphatic amino acid of from 3 to 5 carbon atoms, particularly polar, having an hydroxyl or amide substituent, or acidic;

$aa^{55}$ is a neutral aliphatic amino acid of from 2 to 6 carbon atoms, either non-polar, particularly of from 4 to 6 carbon atoms, or polar of from 4 to 5 carbon atoms having a carboxamide functionality;

$aa^{57}$ is an aliphatic amino acid of from 2 to 6 carbon atoms, particularly non-polar of from 2 to 3 carbon atoms, or a basic amino acid;

$aa^{59}$ is an aliphatic amino acid of from 2 to 6, usually 4 to 6 carbon atoms, usually non-polar, or basic;

$aa^{60}$ is an aliphatic or aromatic amino acid, particularly if aliphatic of from 4 to 6 carbon atoms;

$aa^{64a}$ is a bond or an aliphatic polar amino acid of from 4 to 5 carbon atoms, particularly carboxamide substituted;

$aa^{68}$ is an aliphatic amino acid of from 2 to 6 carbon atoms, particularly non-polar;

$X^4$ is an hydroxyl, alkoxyl of from 1 to 3 carbon atoms, amino, or an amino acid sequence of from 1 to 4, usually 1 to 2, amino acids, particularly aliphatic amino acids, more particularly polar and acidic amino acids, having from 0 to 1 non-polar amino acid of from 2 to 3 carbon atoms, from 0 to 3 acidic amino acids, and from 0 to 3 hydroxyl substituted aliphatic amino acids, wherein $X^4$ may terminate the molecule or be a link to an antigen or immunoglobulin.

Of particular interest is where the symbols have the following definitions:

$aa^{40,56}$—D, E, N, Q;

$aa^{41,42,51,53,63,64,67}$—V, L, or I;

$aa^{47}$—N, Q, S, T, D, E;

aa$^{55}$—N, O, P, L, I, V, particularly P or L;
aa$^{57}$—G, A, K or R;
aa$^{45,59}$—V, L, I, K, R;
aa$^{60}$—V, L, I, F, H, Y;
aa$^{64a}$—bond, N or Q;
aa$^{68}$—G, A, P, L, I, V;
X$^4$—(G, A, D, or E)$_a$—(S, T, D, A, G or E)$_a$—(D or E)$_c$—(T or S)$_a$;
a is 0 or 1; and
c is 0 to 2.

Desirably, $M_R$ will include a sequence of at least about 15 amino acids included in the following wherein:

aa$^{23}$ is an aromatic amino acid or an aliphatic polar amino acid of from 3 to 5 carbon atoms, particularly an amide substituted amino acid;

aa$^{24}$ is an aliphatic non-polar amino acid of from 2 to 6, usually 5 to 6 carbon atoms;

aa$^{25}$ is an aliphatic polar amino acid of from 3 to 5 carbon atoms, particularly an amide or hydroxyl substituted amino acid;

aa$^{27,29,30}$ are aliphatic non-polar amino acids of from 5 to 6 carbon atoms;

aa$^{31}$ is an aliphatic amino acid of from 2 to 6 carbon atoms, either non-polar of from 2 to 3 carbon atoms, or basic;

aa$^{32}$ is an aliphatic amino acid of from 2 to 6 carbon atoms, either non-polar of from 2 to 3 carbon atoms, or basic;

aa$^{34}$ is an aliphatic amino acid of from 3 to 6, usually 3 to 5 carbon atoms, which is non-polar or polar, particularly hydroxyl substituted;

aa$^{37}$ is an aliphatic amino acid of from 2 to 6, usually 3 to 5 carbon atoms, which is non-polar or polar, particularly proline or carboxamide substituted;

aa$^{38}$ is an aliphatic polar amino acid of from 3 to 5 carbon atoms, usually amide or hydroxyl substituted;

aa$^{39}$ is an aliphatic non-polar amino acid of from 2 to 6 carbon atoms;

aa$^{40}$ is an aliphatic acidic amino acid or amide thereof of from 4 to 5 carbon atoms;

aa$^{41}$ is a non-polar aliphatic amino acid of from 5 to 6 carbon atoms; and

X$^5$ is a bond, hydroxyl, alkoxy of from 1 to 3 carbon atoms, wherein X$^5$ may terminate the sequence, be a link to $B_{aR}$ or to an antigen.

Of particular interest are the following definitions for the symbols:
aa$^{23}$—F, H, Y, N, Q;
aa$^{24,27,29,30,41}$—V, L, I;
aa$^{25,38}$—S, T, N, Q;
aa$^{31,32}$—G, A, K, R;
aa$^{34}$—P, S, T;
aa$^{37}$—P, N, Q;
aa$^{38}$—S, T, N, Q;
aa$^{39}$—G, A, P, V, L, I;
aa$^{40}$—D, E, N, Q; and
aa$^{41}$—V, K, or U As is evident from the above formulas, various conservative substitutions can be made in the above sequences without significantly affecting the physiological activity of the polypeptide. Also, deletions and insertions of from 1 to 2 amino acids may be employed. Usually, not more than 5, usually not more than 3, changes (substitution, deletion or insertion) will be made in the above sequence.

Of particular interest for use in the subject invention are compounds having the following sequence:
E-A-E-E-D-G-D-L-Q-C-L-C-V-K-T-T-S-Q-V-R-P-R-
-H-I-T-S-L-E-V-I-K-A-G-P-H-C-P-T-A-Q-L-I-A-T-
L-K-N-G-R-K-I-C-L-D-L-Q-A-P-L-Y-K-K-I-I-K-
K-L-L-E-S or analogs thereof, particularly analogs or fragments which include the four C residues at approximately their respective positions and the 12 amino acids at or proximal to the C-terminus, particularly the 10 amino acids proximal to the C-terminus, and more particularly the 8 amino acids proximal to the C-terminus which includes four basic and four neutral aliphatic amino acids. Analogs of the above composition will usually have at least about 80%, more usually at least about 85%, and preferably at least about 90% of the same amino acids in the above sequence or portion of the above sequence.

Preparation of Platelet Factor 4 and Congeners

The naturally occurring polypeptide compositions employed in this invention can be obtained in high purity as established by sensitive bioassays. The naturally occurring polypeptide compositions will have less than about 20%, more usually less than about 10%, and preferably less than about 5% by weight of polypeptides other than the major constituent present in the composition, which contaminating polypeptides are associated with platelets.

Platelet factor 4 can be obtained by extraction of platelets with approximately 0.3 M ethanolic hydrochloric acid. As inhibitors against degradation, phenylmethylsulfonyl fluoride and aprotinin may also be included, the former at concentrations of about 1–10% by weight of the extracting composition and the latter at concentrations of about 0.1–1 TIU/mg (TIU—trypsin inhibition units) of the extracting composition. After raising the pH to about 5, using aqueous ammonium hydroxide, a small amount of ammonium acetate is added and the solution clarified by centrifugation or other convenient means.

The protein is then precipitated by employing in tandem cold ethanol (95%) and ether, the precipitate collected and dialyzed against 0.1–0.5 M acetic acid employing a dialysis membrane having a cutoff below about 3,000 Mr. The residue is lyophilized, resuspended in 1 M acetic acid, clarified and is then ready for further purification by gel permeation chromatography employing Biogel P-10. The product is eluted with about 1 M acetic acid and the various fractions monitored employing an appropriate assay technique, e.g., tumor growth inhibition.

The fractions having the growth inhibiting activity are lyophilized, resuspended in dilute aqueous trifluoroacetic acid (TFA), pH 2–3, clarified and then chromatographed on a high pressure liquid chromatograph (HPLC), where the silica packing has a coating of a long aliphatic chain of from about 16 to 20 carbon atoms, e.g., 18 carbon atoms. The column is equilibrated with dilute TFA (0.02–0.1%) and the product eluted with an acetonitrile gradient of up to 60% acetonitrile in dilute (0.01–0.1, usually about 0.04–0.05%) TFA. A relatively slow flow rate is employed, generally about 0.5 to 1 ml/min. at ambient temperatures. The fractions may be assayed by the tumor growth inhibition assay or other bioassay. For further purification, the product obtained from the column may be purified utilizing high pressure gel exclusion chromatography.

The major peak of platelet factor 4 activity resolved by Novapak $C_{18}$ reversed phase HPLC is lyophilized and resuspended in 100 μl of 40% acetonitrile containing 0.1% TFA. The sample is injected into a hydroxylated polyether gel column (BioRad TSK-250) and eluted with a mobile phase consisting of 40% acetonitrile in 0.1% TFA. Aliquots of each fraction are lyophilized and tested for platelet factor 4 activity; tumor cell inhibition activity coelutes with the major peptide peak ($R_f$-0.9), which also corresponds in molecular weight to that of the 6,000 Mr insulin marker used to calibrate this chromatographic system.

The product obtained from the column may be electrophoresed employing SDS-PAGE. The band at about 6,000–8,000 molecular weight is isolated. The band is shown to have strong growth inhibitory activity against neoplastic mammalian cells.

Instead of isolating platelet factor 4 from natural sources or synthesizing the polypeptide or its congeners on a solid support, platelet factor 4 and fragments or analogs thereof as well as fusion proteins in which platelet factor 4 is fused to, for example, a leader sequence from a prokaryotic gene, may be prepared by hybrid DNA technology. The structural gene for platelet factor 4 can be obtained from the host cell genome employing probes prepared based on the amino acid sequence. A genomic library may be searched using the probe (which may be appropriately redundant), hybridizing the fragments isolated and the fragments reduced in size and characterized by restriction mapping and sequencing.

Alternatively, a cDNA library may be searched analogously to the genomic library and if complete or partial structural genes are isolated these can be used, the latter by employing an adapter to replace any missing codons.

Conveniently, a synthetic gene may be synthesized. By employing a synthetic gene substantial flexibility is achieved in that host preferred codons may be employed and unique or rare restriction sites may be introduced. The restriction sites add a degree of flexibility in modifying various portions of the gene, introducing deletions, transitions, transversions, insertions, and the like. A strategy is devised employing single-stranded overlapping fragments which can be mixed together in a hybridizing ligating medium without interfering heteroduplex formation. The resulting double-stranded gene may then be cloned and purified. An exemplary sequence is set forth in the experimental section.

Desirably, the termini of the gene are different to ensure proper orientation upon insertion. The gene may be inserted into an appropriate expression vector for expression. A large number of vectors are available for expression in prokaryotes and eukaryotes, such as fungi, e.g., yeast, mammalian cells, e.g., mouse cells, primate cells, etc. The replication system may be derived from plasmids, viruses or chromosomes. Illustrative replication systems include ColE1, λ, RSF1010, 2 μm plasmid, SV40, adenovirus, papilloma bovine virus, baculovirus, etc.

Once a complete gene has been identified, either as cDNA or chromosomal DNA, it may then be manipulated in a variety of ways to provide for expression. Both prokaryotic and eukaryotic hosts may be employed, which may include bacteria, yeast, insect cells, and mammalian cells, e.g. *E. coli* COS cells, CHO cells, monkey kidney cells, and silkworm cells (sf9). Therefore, where the gene is to be expressed in a host which recognizes the wild-type transcriptional and translational regulatory regions of Oncostatin M, the entire gene with its wild-type 5'- and 3'-regulatory regions may be introduced into an appropriate expression vector. Various expression vectors exist employing replication systems from mammalian viruses, such as Simian Virus 40, adenovirus, bovine papilloma virus, vaccinia virus, insect baculovirus, etc. These replication systems have been developed to provide for markers which allow for selection of transfectants, as well as providing for convenient restriction sites into which the gene may be inserted.

Where the gene is to be expressed in a host which does not recognize the naturally occurring wildtype transcriptional and translational regulatory regions, further manipulation will be required. Conveniently, a variety of 3'-transcriptional regulatory regions are known and may be inserted downstream from the stop codons. The non-coding 5'-region upstream from the structural gene may be removed by endonuclease restriction, Ba131 resection, or the like. Alternatively, where a convenient restriction site is present near the 5'-terminus of the structural gene, the structural gene may be restricted and an adaptor employed for linking the structural gene to the promoter region, where the adaptor provides for the lost nucleotides of the structural gene. Various strategies may be employed for providing for an expression cassette, which in the 5'-3'-direction of transcription has a transcriptional regulatory region and a translational initiation region, which may also include regulatory sequences allowing for the induction of regulation; the structural gene under the transcriptional and translational control of the initiation region; and a transcriptional and translational termination region.

Choice of appropriate regulatory sequences will take into account the following factors which affect expression. In terms of transcriptional regulation, the amount and stability of messenger RNA are important factors which influence the expression of gene products. The amount of mRNA is determined by the copy number of the particular gene, the relative efficiency of its promoter and the factors which regulate the promoter, such as enhancers or repressors. The stability of the mRNA is governed by the susceptibility of the mRNA to ribonuclease enzymes. In general, exonuclease digestion is inhibited by the presence of structural motifs at the ends of the mRNA; palindromic structures, altered nucleotides, or specific nucleotide sequences. Endonuclease digestion is believed to occur at specific recognition sites within the MRNA and stable mRNAs would lack these sites. There is also some evidence that mRNAs undergoing high levels of translation are also protected from degradation by the presence of ribosomes on the mRNA.

In terms of translational regulation, given the presence of mRNA, expression can be regulated by influencing the rate of initiation (ribosome binding to the mRNA), the rate of elongation (translocation of the ribosome across the mRNA), the rate of post-translational modifications and the stability of the gene product. The rate of elongation is probably affected by codon usage, in that the use of codons for rare tRNAs may reduce the translation rate. Initiation is believed to occur in the region just upstream of the beginning of the coding sequence. In prokaryotes, in most cases this region contains a consensus nucleotide sequence of AGGA, termed the Shine-Dalgarno sequence. While this sequence characterizes the ribosomal binding site, it is evident that both sequences upstream and downstream can influence successful initiation. Translational enhancer sequences have been detected which regulate expression. Evidence also points to the presence of nucleotide sequences within the coding region which can affect ribosome binding, possibly by the formation of structural motifs through which the ribosome recognizes the initiation site. Position of the AGGA sequence with respect to the initiating ATG codon can influence expression. It is thus the interaction of all of these factors which determines a particular expression rate. Highly expressed genes have evolved a combination of all of these factors to yield a particular rate of expression. Design of an expression system to yield high levels of gene product must take into consideration not only the particular regions that have been determined to influence expression, but also how these regions (and thus their sequences) influence each other.

Illustrative transcriptional regulatory regions or promoters include, for bacteria, the β-gal promoter, the TAC promoter, lambda left and right promoters, trp and lac promoters, trp-lac fusion promoter, etc.; for yeast, glycolytic enzyme promoters, such as ADH-I and -II promoters, GPK promoter, and PGI promoter, TRP promoter, etc.; for mammalian cells, SV40 early and late promoters, adenovirus major late promoters, etc.

The transcriptional regulatory region may additionally include regulatory sequences which allow the time of expression of the structural gene to be modulated, e.g. by presence or absence of nutrients or expression products in the growth medium, temperature, etc. For example, expression of the structural gene may be regulated by temperature using a regulatory sequence comprising the bacteriophage lambda $P_L$ promoter, the bacteriophage lambda $O_L$ operator and the CI857 temperature-sensitive repressor. Regulation of the promoter is achieved through interaction between the repressor and the operator.

The expression cassette may be included within a replication system for episomal maintenance in an appropriate cellular host or may be provided without a replication system, where it may become integrated into the host genome. The DNA may be introduced into the host in accordance with known techniques, such as transformation, using calcium phosphate-precipitated DNA, transfection by contacting the cells with the virus, microinjection of the DNA into cells or the like.

Once the structural gene has been introduced into the appropriate host, the host may be grown to express the structural gene. In some instances, it may be desirable to provide for a signal sequence (secretory leader) upstream from and in reading frame with the structural gene, which provides for secretion of the structural gene. Illustrative secretory leaders which have been described include the secretory leaders of penicillinase, α-factor, immunoglobulins, T-cell receptors, outer membrane proteins, and the like. By fusion in proper reading frame the mature platelet factor 4 or congener may be secreted into the medium.

Additional amino acids may be inserted between the structural gene and the leader sequence which provides an enzymatic or chemical cleavage site for cleavage of the secretory leader, so as to provide for the mature polypeptide in the supernatant. Alternatively, the fusion protein comprising the secretory leader sequence and the structural gene product may find use without cleavage of the mature polypeptide. In addition, a cytotoxic agent such as a toxin A-chain fragment or a targeting molecule such as a hormone or antibody can be coupled covalently to the leader sequence, with minimal effect on the biological activity of the structural gene product.

The construct containing the structural gene and flanking regions providing regulation of expression may be introduced into the expression host by any convenient means, e.g., transformation, with for example, calcium phosphate precipitated DNA, transfection, transduction, conjugation, microinjection, etc. The host may then be grown to a high density in an appropriate nutrient medium. Where the promoter is inducible, permissive conditions will then be employed, e.g., temperature change, exhaustion or excess of a metabolic product or nutrient, or the like.

Where the product is retained in the host cell, the cells are harvested, lysed and the product isolated and purified by extraction, precipitation, chromatography, electrophoresis, etc. Where the product is secreted, the nutrient medium may be collected and the product isolated by conventional ways, e.g., affinity chromatography.

The recombinant products may be glycosylated or non-glycosylated, having the wild-type or other glycosylation. In general, the glycosylation will differ by not more than about 50% usually by not more than about 20% from the wild-type glycosylation. The amount of glycosylation will depend in part upon the sequence of the particular peptide, as well as the organism in which it is produced. Thus expression of the product in *E. coli* cells will result in an unglycosylated product, and expression of the product in insect cells generally will result in less glycosylation than expression of the product in mammalian cells.

Uses for Platelet Factor 4 and Congeners

The polypeptide compositions of this invention demonstrate a variety of physiological activities. The subject compositions can be used to inhibit tumor growth in vitro and in vivo. The subject compositions can also be used to stimulate autophosphorylation of pp60 src. Subject compositions may thus serve as a substrate for the pp60 src enzyme and can be phosphorylated at the tyrosine position (residue 60) in the polypeptide. Also, tumor cells can be induced to release a 52 kD (p52) protein when treated with platelet factor 4. In addition, platelet factor 4 or analogs, fragments thereof, or fusion proteins containing subsequences (fragments) having competitive immunological properties can be used to produce monoclonal antibodies or act as a reagent in diagnostic assays for the detection of platelet factor 4 or immunologically competitive compounds or the presence of cell surface receptors for platelet factor 4.

The subject compounds have high activity for tumor inhibition. The subject compositions can be used in vitro or in vivo for reducing the rate of growth of neoplastic cells. The polypeptide compositions can provide at 1 ng levels at least about 20% inhibition of tumor cell growth, particularly of carcinomas and sarcomas, e.g., of the lung, breast, skin, etc. Preferably the polypeptide compositions will provide at least about 40%, and more preferably at least about 50%, inhibition of tumor cell growth in accordance with the colony inhibition test described in the Experimental section.

The subject compositions can be used in vivo by being administered to a host suspected of having neoplasia. The subject compositions can be applied to a neoplastic site, e.g., a melanoma, to reduce the rate of proliferation. Methods of application may include injection, introduction by catheter, direct application, or the like, depending upon the site of the tumor, the formulation of the subject composition, the dosage level and the like. Dosage will vary depending upon whether it is systemic or local, with dosage concentrations generally being from about 0.1 µg to 1,000 µg/Kg and total dosages for large mammals including primates of from about 0.01 to 10 mg per treatment dose.

Platelet factor 4-like materials, including platelet factor 4 and its congeners, can be formulated in physiologically acceptable carriers, such as phosphate buffered saline, distilled water, excipients, or the like, or may be employed neat.

Platelet factor 4 and its congeners may be employed indirectly for detecting the presence of neoplastic cells. Where tumor cells are subjected to concentrations of the active agent of from about 1 to 500 ng/ml, preferably from about 50 to 350 ng/ml of the active agent, p52 is secreted. Thus, one could detect the presence of neoplastic cells by detecting the secretion of p52 into the external medium, e.g., nutrient medium, blood, urine or other physiological fluid. Platelet factor 4 can therefore be used to monitor the state of a host and the existence or absence of a neoplastic condition. Platelet factor 4 can be used in diagnosing whether a tumor exists in monitoring surgery, levels of metastasis, or the like. The platelet factor 4-like substance would be administered in vitro or in vivo (culture medium or host) in a sufficient amount to provide for induction of the secretion of p52. Fluid associated with the system would then be monitored for the presence of p52 as an indication of the presence of neoplastic cells.

Platelet factor 4-like materials can also be used to stimulate the immune system, either by itself, but preferably in conjunction with other lymphokines, e.g., interferon, more particularly γ-interferon. Thus, the platelet factor 4-like materials may be formulated with other polypeptides and administered to a host which is immunosuppressed, so as to stimulate the immune system. Gamma-interferon is known to induce Ia expression in monocutes and macrophages, as well as other tissues, such as endothelium and fibroblasts. The platelet factor 4-like materials induce Ia expression and stimulate the γ-interferon Ia induction, enhancing the efficacy of a given dose of γ-interferon. The amount of platelet factor 4-like materials will generally be employed to provide a concentration in the medium in the range of about 1 to 200, preferably about 2 to 70 ng/ml. The amount of γ-interferon will be conventional as to its use as a lymphokine, generally being in the range of about 0.5 to 200 ng/ml. Enhancements in expression of Ia of at least about 1.5, usually at least 2-fold, can be achieved with platelet factor 4-like materials, when used by itself or in conjunction with other lymphokines. Administration may be employed as described previously.

The platelet factor 4-like materials can also be used in conjunction with kinases, particularly pp60 src to change the substrate specificity of the enzyme. Particularly, by contacting the enzyme with small amounts of an platelet factor 4-like material, particularly at concentrations of from about 0.05 to 50 #µg/ml, the kinase activity may be enhanced, including a change in the observed amino acids which are phosphorylated, particularly, besides tyrosine being phosphorylated, serine is also phosphorylated. In this way, the combination of pp60 src or analogous kinases may be used for modifying polypeptides having tyrosine and serine amino acids, by providing for phosphorylation of both tyrosine and serine at enhanced rates.

The subject platelet factor 4-like materials may also be used as haptens or antigens, as haptens linked to an immunogenic potentiator, e.g., an antigen, particle or the like, for production of monoclonal antibodies or polyclonal sera. The antibodies can find wide use, particularly for diagnostic purposes. The antibodies may be used by themselves or in conjunction with platelet factor 4-like materials as reagents for the detection of platelet factor 4 and platelet factor 4 receptors, including antibodies to platelet factor 4.

A wide variety of protocols and techniques are available for determining analytes of interest. These techniques involve a wide variety of labels, including enzymes, radionuclides, fluorescers, chemiluminescers, enzyme substrates, enzyme inhibitors, particles, and the like. The methods may involve a separation step (heterogeneous) or no separation step (homogeneous). The label may be covalently bonded to either the platelet factor 4-like material or the antibody to platelet factor 4 (anti-platelet factor 4) or may be conjugated to an antibody directed to the anti-platelet factor 4, for example to the Fc of the anti-platelet factor 4. The whole antibody may be used or fragments thereof, including Fab, F(ab)'₂, Fv, or the like. A number of United States patents have issued describing a wide variety of diagnostic techniques which may be used in this invention. Exemplary of these patents are U.S. Pat. Nos. 3,766,162; 3,791,932; 3,817,837; 3,996,345; and 4,233,402. Particular types of assays include RIA, EIA, EMIT (Registered Trademark), ELISA, SLFIA, FIA, all of which have found commercial application and for which reagents are available for other analytes. The various reagents may be provided in kits where the nature of the reagents and their relative amounts are selected for optimizing the sensitivity of the assay.

The antibodies may be prepared in conventional ways in accordance with the preparation of monoclonal antibodies or polyclonal sera. In each instance, an appropriate host will be injected with an immunogen having one or more epitopic site(s) of interest, usually followed by one or more booster injections. For polyclonal antisera, the host may be bled and the globulin fraction isolated. The globulin fraction may be further purified by affinity chromatographay. For monoclonal antibodies, the host will be immunized as before, but in this instance the spleen will normally be removed and fused with an appropriate fusion partner. After selection of hybridomas expressing the desired antibody, the hybridomas will be subjected to limiting dilution, followed by selection and cloning, and further characterization.

The antibodies according to this invention may be of any of the types which naturally occur, such as IgA, IgD, IgE, and IgM, particularly IgM and the various subtypes of IgG, i.e., IgG1, 2, 3 or 4.

The resulting monoclonal antibodies can be used as immunogens for production of anti-idiotype antibodies which will have conformational similarity to the platelet factor 4 type materials. These may then be used as substitute reagents for platelet factor 4 type materials in a variety of applications.

Besides being used for expression the structural gene sequences may be used as probes for hybridization and detection of duplexing sequences. For example, the presence and amount of MRNA may be detected in host cells.

The following examples are offered by way of illustration and not by way of limitation.

EXPERIMENTAL

Abbreviations: DMEM=Dulbeccol's modified eagle's medium; PBS=phosphate buffered saline; P/S=penicillin/streptomycin (0.57 mg/ml each); FCS=fetal calf serum; SDS-PAGE=sodium dodecylsulfate polyacrylamide gel electrophoresis.

Table of Contents

Example 1:
Bioassay Protocols
A. Inhibition of DNA Synthesis
B. Soft Agar Colony Inhibition
C. Inhibition of Tumor Growth in Nude Mice
E. Stimulation of pp60 src Autophosphorylation
F. Macrophage Ia Antigen Expression
Example 2:
Isolation of Platelet Factor 4 from Human Platelets
A. Acid-ethanol Extraction from Human Platelets
B. Gel Permeation Chromatography
C. Reversed Phase High-pressure Liquid Chromatography
Example 3:
Biological Activity of Platelet Factor 4 Isolated from Human Platelets
A. Inhibition of DNA Synthesis
B. Soft Agar Colony Growth Inhibition
C. Inhibition of Tumor Growth in Nude Mice
D. Specific Release of $M_r$ 52K polypeptide
E. Stimulation of pp60 src Autophosphorylation
Example 4:
Production of Monoclonal and Polyclonal Antibodies Specific for Platelet Factor 4
A. Cross-linking Platelet Factor 4 to Bacteria Lipopolysaccharide
B. In Vitro Immunization of Balb/C Splenocytes with Platelet Factor 4 and LPS Conjugate
C. Production of Monoclonal Antibodies
D. ELISA Assay for Platelet Factor 4
E. Production of Polyclonal Anti-Platelet Factor 4 Antiserum
Example 5:
Preparation of Synthetic Platelet Factor 4 Oligonucleotides
A. Synthesis of Platelet Factor 4 Gene
B. Description of Cloning and Expression Plasmids
C. Preparation of Recombinant Platelet Factor 4 Genes
Example 6:
Preparation of Recombinant Platelet Factor 4
A. Isolation of PF4 Expressed in Recombinant Bacteria
Example 7:
Biological Activity of Platelet Factor 4 Prepared in Prokaryotic Cells
A. Inhibition of DNA Synthesis
B. Inhibition of Growth of Tumors in Nude Mice

EXAMPLE 1

Bioassay Protocols

A. Inhibition of DNA synthesis

On day 2 in the morning A549 cells (human lung carcinoma) in Nunc 96-well plates (Kamstrupvej 90. DK4,000, Roskilde, Denmark) were set up. These cells were passaged when there were fewer than 30. Into all but the peripheral wells was introduced $4 \times 10^3$ cells/50 $\mu$l/well ($9 \times 10^4$ cells/ml assay medium (DMEM) with 10% FCS, P/S, glutamine). The peripheral wells received 50 $\mu$l PBS and the entire plate was incubated at 37° C. In the afternoon, the test compounds were resuspended in assay medium. All compounds were tested in triplicate. Into each test well was delivered 50 $\mu$l of test compound in assay medium, while control wells received 50 $\mu$l assay medium alone. Each plate was then incubated at 370° C. for 3 days. On day 4, into each well 50 $\mu$l of a solution of $^{125}$I-iodo-21'-deoxyuridine (4 Ci/mg to 0.5 mCi/ml) (1 $\mu$l isotope/ml assay medium) was added and the plates incubated at 370° C. overnight. On day 5, the medium was aspirated from the wells, and the wells washed 1X with PBS. One hundred microliters of methanol were added for 10 min at room temperature. The methanol was aspirated and 200 $\mu$l of 1 M sodium hydroxide were added to each well. The plate was incubated for 30 min at 370° C., and the sodium hydroxide removed with Titertek plugs (Flow Labs). The plugs were then counted in a gamma counter.

B. Soft Agar Colony Inhibition

The materials employed were 5% agar (3.75 g Nobel agar (Difco)), 75 ml of distilled water autoclaved in a 125 ml Wheaton bottle, DMEM with 10% FCS, 100 U penicillin, 100 U streptomycin, 200 mM glutamine, and human melanoma cells (A375).

Materials to be tested were lyophilized in a sterile 12×75 mm test tube. A 1:10 dilution of the 5% agar was made with DMEM and heated to 460° C. in a water bath. A base layer was prepared by pipetting 1 ml of 0.5% agar solution into each well of a 6-well culture plate (35×14 mm). The layer was allowed to stand at room temperature until it hardened. SA$_6$ cells were prepared by trypsinizing and the number of cells counted. The cells were diluted to a final concentration of $1 \times 10$ cells/ml and 0.35 ml of cells were added to each test sample tube.

Into each of ten test sample tubes was pipetted 0.750 ml of a 0.5% agar solution. The mixture was vortexed gently and the contents of the test sample tube (test sample, cells, agar) were poured onto the base layer and allowed to stand for about 20 min at room temperature until the agar hardened. The plates were then incubated in a 370° C. humidified incubator with 5% carbon dioxide/ 95% air.

The plates were checked for inhibition of colony growth after 3 days and up to 10 days depending on the potency of the test material. The number of colonies was counted in 8 random low power microscope fields. When plates were to be maintained longer than 5 days, an additional 1 ml layer of 0.3% agar solution was overlayed on the test sample layer to prevent drying of the test sample layer.

C. Inhibition of Tumor Growth in Nude Mice

Male nude mice (Balb/c-nu+/nu+) were supplied by the Fred Hutchinson Cancer Research Center, Seattle, WA. At 12 weeks of age, mice were given injections (s.c. in the neck region with approximately 1.3×10⁶ human lung carcinoma cells (A549) in a volume of 0.2 ml of phosphate-buffered saline. Palpable tumors (approx. 10 mm³) usually developed in 20 days. Each group contained 5 animals. Animals were injected every two or three days at the tumor site with 0.1 ml of PBS (control group) or test sample (1.2 μg/injection) resuspended in 0.1 ml of PBS. Day one post-treatment corresponds to the first day animals were injected at the tumor site with test compounds. Tumor size was measured before subsequent injection on the days indicated and represents the average size of tumor in each animal in the group.

D. Specific Release of a 52,000 Mr Polypeptide

Human lung carcinoma cells (A549) or other cell line were treated with a test sample (200 ng/ml of culture) or PBS and the effect on polypeptides released into the cell culture supernatant was determined. Treated and control cultures (no platelet factor 4) were pulsed with ³⁵S-methionine (5 μCi/ml S.A. - 800 Ci/mMol) at time 0 (addition of platelet factor 4 or medium only (control)). Twelve hours later culture supernatants were removed and clarified, first at low speed (1,500×g for 15 min) then at high speed (30,000×g for 1 hr). Polypeptides were precipitated from clarified supernatants with trichloroacetic acid (TCA) followed by SDS-PAGE on 12.5% polyacrylamide slab gels.

Radioautography of the gel was then used to determine the presence of a 52,000 Mr ³⁵S-methionine labeled polypeptide in supernatants derived from A549 cells treated with the test sample.

E. Stimulation of pp60 src Autophosphorylation pp60 src was purified by immunoaffinity chromatography as described (Erickson et al., *Proc. Natl. Acad. Sci. USA* (1979) 76:6260-6264; Erickson et al., *Cold Spring Harbor Symp. Quant. Biol.* (1979) 44:902-917. Five microliters of purified enzyme (approximately 0.47 pM) were incubated with 100 ng of test sample or PBS in a final reaction volume of 30 μl containing 20 mM ATP, 5 mM MgCl₂, 10 mM Tris-Cl, pH 7.2 for 30 min at 30° C. Reactions were terminated by the addition of 2X sample buffer and analyzed by SDS-PAGE as described (Laemmeli, *Nature* (1970) 227:680-685).

F. Macrophage Ia Antigen Expression

Wehi-3 is a mouse macrophage cell line which can be induced by gamma interferon (γ-IFN) to express H2 Class II antigens. The features of this induction have been studied by several laboratories and shown to be an accurate replica of normal macrophage induction. These cells were grown either with or without a low concentration of γ-IFN and with one of several concentrations of the sample to be tested. Both in the presence and absence of γ-IFN, platelet factor 4 showed a dose-dependent enhancement of Class II antigen as measured by direct immunofluorescence on a fluorescent activated cell sorter (FACS). The magnitude of the platelet factor 4 effect was generally (~2-70 ng/ml).

EXAMPLE 2

Isolation of Platelet Factor 4 from Human Platelets

A. Acid-ethanol Extraction from Human Platelets

Fresh or frozen platelets (50 g wet weight) thawed at room temperature were resuspended in two volumes of: 375 ml ethanol (95%), 7.5 ml conc. HCl, 33 mg phenylmethylsulfonyl fluoride and 1 ml of aprotinin (23 TI-U/ml; from bovine lung, Sigma Chemical Co. A6012). The mixture was stirred at 4° C. overnight, centrifuged at 8,000 rpm in a Beckman-type 19 rotor for 30 min and the supernatant removed. The pH of the supernatant was adjusted with conc. ammonium hydroxide to 4.0 and the pH raised to 5.2 using a 1:10 dilution of conc. ammonium hydroxide. After adding 1 ml of 2 M ammonium acetate (pH 5.2) per 0.1 of supernatant, the solution was centrifuged at 8,000 rpm in a type 19 rotor for 30 min. The supernatant was removed, a 2X volume cold 95% ethanol added, followed by 4X volume cold diethyl ether and the mixture allowed to stand overnight at 0° C. The precipitate was collected by centrifuging at 8,000 rpm in a type 19 rotor for 30 min and the pellet was suspended in about 10-20 ml of 1 M acetic acid. The acetic acid dispersion was dialyzed extensively against 5 1 ×2 changes of 0.2 M acetic acid in a Spectrapor dialysis membrane (#3) tubing (cutoff 3,500 Mr) (American Scientific Products). The extract was lyophilized, resuspended in 7.5 ml of 1 M acetic acid, followed by centrifuging at 30,000 rpm.

B. Gel Permeation Chromatography

Biogel P-10 (200-400 mesh; BioRad Labs) was swelled overnight in 1 M acetic acid, degassed thoroughly and then poured into a 100×2.5 cm siliconized glass column and allowed to equilibrate overnight with 1 M acetic acid. All solutions were degassed before using.

The acid-ethanol solubilized peptides (50-70 mg of protein) from 25 g of human platelets were dissolved in 7.5 ml of 1 M acetic acid and applied to the above column. Fractions (3.5 ml) were collected and aliquots were lyophilized and tested for inhibition of 5-¹²⁵I-iodo-2'-deoxyuridine incorporation into A549 human lung carcinoma cells.

C. Reversed-phase High-pressure Liquid Chromatography

The fraction containing the peak of tumor growth inhibitory activity (about 200 ng of protein) from the above column was lyophilized and resuspended in 0.05% (v/v) of TFA. The column was then eluted with a linear 0.60% gradient of acetonitrile in 0.045% TFA at a flow rate of 0.8 ml/min at 23° C. Aliquots of each fraction were lyophilized and assayed in triplicate, as described above.

The fraction(s) containing the inhibitory activity were then dissolved in 40% acetonitrile containing 0.1% TFA and applied to a hydroxylated polyether gel column (BioRad TSK-250) and eluted with a mobile phase of 40% acetonitrile in 0.1% TFA. Fractions were collected, lyophilized, and assayed in triplicate for growth inhibitory activity. The activity elutes in the fraction where the insulin marker elutes and corresponds to a molecular weight of 6-8 kD.

Those fractions having the highest activity were then electrophoresed employing SDS-PAGE as follows. The peptide corresponding to the major platelet factor 4 activity from the reversed phase HPLC purification step was lyophilized, resuspended and boiled (2 min) in 0.03 ml of a sample preparation buffer containing 12.5 mM Tris-Cl, pH 6.7, 4% SDS, 10% β-mercaptoethanol, 20%. glycerol and 0.01% bromphenol blue. The sample was loaded onto a 5% polyacrylamide stacking gel poured over a 17 to 27% polyacrylamide gradient slab gel containing 0.1% SDS, at pH 8.8. The gel was run at 10 milliamps until samples migrated through the stacking gel and at 20 milliamps until the dye front migrated to the bottom of the gel. Gels were fixed and stained overnight in a solution of 0.2% Coomassie blue, 50% methanol and 9% acetic acid. Following destaining, Coomassie positive bands were localized utilizing a Hoffer densitometer. Markers included insulin (6,000 Mr), trypsinogen (24,500 Mr), RNase (13,700 Mr), and aprotinin (6,500 Mr). The major peptide comigrated with the 6,500 Mr aprotinin standard under these conditions of electrophoresis.

EXAMPLE 3

Biological Activity of Platelet Factor 4 Isolated from Human Platelets

A. Inhibition of DNA synthesis

The effect of platelet factor 4 on DNA synthesis was tested using a number of cell lines, both transformed and non-transformed using the assay described in Example 1A, above. The subject compound inhibited a variety of cultured human tumor cells, but not normal non-transformed human foreskin fibroblasts, as shown in the following table.

TABLE I

Effect of Platelet Factor 4 on in vitro DNA Synthesis in Cultured Human Cells

| Cell Line | % Maximal* Inhibition $^{125}$I-deoxyuridine Incorporation |
|---|---|
| Transformed | |
| Human carcinoma of lung (A549) | 100 |
| Human adenocarcinoma of lung (H125) | 41 |
| Human melanoma (A375) | 67 |
| Human carcinoma of breast (MCF-7) | 37 |
| Non-transformed | |
| Human foreskin fibroblast (HuF$_{p6}$) | 0 |

*Using the assay, conditions described, the maximum inhibition of $^{125}$I-deoxyuridine incorporation into A549 cells observed at saturating concentrations of platelet factor 4 (≈100 ng/well) does not exceed 50% relative to untreated control cultures.

B. Soft Agar Colony Growth Inhibition

The above procedure was employed using varying concentrations of purified platelet factor 4. The following table indicates the results, the amount of platelet factor 4 indicated being the lyophilized amount introduced into the test tube. The results are reported as percent maximal inhibition.

TABLE II

| Platelet Factor 4 (ng) | % Maximal Inhibition |
|---|---|
| 0.8 | 45 |
| 2.6 | 73 |
| 20.0 | 81 |
| 60.0 | 100 |

It is evident from the above results, that the subject polypeptide is a potent inhibitor of cell growth. Based on the results observed with the melanoma cells, about 1 ng is sufficient to provide about 50% inhibition. The subject compound can, therefore, find a wide variety of uses in inhibiting cellular growth, including neoplastic cellular growth.

C. Inhibition of Tumor Growth in Nude Mice

Injection of either bovine serum albumin (0.2 mg) or a synthetic peptide (200 ng) corresponding to a loop region of epidermal growth factor (EGF residues 11-21) in PBS did not inhibit tumor growth.

D. Specific Release of Mr 52K Polypeptide

Human lung cells (A549) were treated with platelet factor 4 as described in Example 1D, above. As analyzed by SDS-PAGE, supernatants from treated cells contained a radiolabeled 52K Mr protein. Untreated cancer cells released minimum amounts of this protein (at least a tenfold increase was seen after platelet factor 4 treatment). No other qualitative or quantitative differences were seen between treated and control cultures.

E. Stimulation of pp60 src Autophosphorylation

Autophosphorylation of pp60 src was analyzed according to the method outlined in Example 1E. Following treatment with platelet factor 4, autoradiography of the slab gels indicated an apparent two-fold stimulation in autophosphorylation of pp60 src. The increase in phosphorylation was not restricted to tyrosine residues but was also found in serine positions in the src enzyme.

EXAMPLE 4

Production of Monoclonal and Polyclonal Antibodies Specific for Platelet Factor 4

A. Cross-linking Platelet Factor 4 to Bacteria Lipopolysaccharide

The procedure for cross-linking platelet factor 4 to bacterial lipopolysaccharide is a modification of the method developed by Primi and Cazenave, J. Immunol. (1982) 1299(3):1124–1129.

Ten ng of platelet factor 4 and 12.5 ng of bacterial lipopolysaccharide (LPS; Sigma #L-263) were diluted to a volume of 500 μl with distilled water. Fifty μl of 2.5% glutaraldehyde in PBS was added and the mixture was incubated for 30 min. at room temperature. The reaction was stopped by adding 50 μl of 2 M glycine in PBS and incubating the mixture at room temperature for 1 hr. The platelet factor 4-LPS conjugate was diluted with 10 ml of mixed lymphocyte conditioned (MLC) medium (see below) then was filter sterilized for use in an in vitro immunization.

B. In Vitro Immunization of Balb/C Splenocytes with Platelet Factor 4 and LPS Conjugate Non-immune splenocytes were immunized using the platelet factor 4-LPS conjugate in vitro by a modification of the procedure described by Reading, Immunol. Meth. (1982) 53:261–269.

MLC medium was prepared by culturing equal numbers (4×10$^6$ cells/ml) of Balb/C and C57 black mouse thymocytes in DMEM containing 2% rabbit serum for 48 hr. The medium was collected and stored at −20° C.

Peritoneal exudate cells (PEC) were collected by flushing a thioglycollate treated Balb/C mouse with sterile PBS. The PEC cells were placed in culture with 1 mouse equivalent of splenocytes and 10 ml of MLC medium containing 10 ng of platelet factor 4-LPS conjugate. The cells were cultured for 7 days.

C. Production of Monoclonal Antibodies

The immunized splenocytes were collected and fused with SP2/0 myeloma cells at a ratio of 1:1 to produce hybridomas which synthesize platelet factor 4 specific monoclonal antibodies. The hybridomas were tested for production of platelet factor 4 antibodies by an enzyme linked immunoassay (ELISA). Positive hybridomas were cloned twice by limiting dilution. Clones were expanded, tested for immunoglobulin class, and injected into Balb/C mice for ascites production.

Forty positive hybridoma clones were initially expanded and retested for anti-platelet factor 4 activity. Seven of the most reactive clones were used to produce ascites fluid in Balb/c mice. The remaining clones were expanded and frozen. The ascites were tested for specificity against platelet factor 4 , an platelet factor 4 peptide-KLH conjugate and BSA in an ELISA. The ascites reacted with both platelet factor 4 and to a lesser extent the platelet factor 4 peptide at dilutions of 1 to 3,000.

The immunoglobulins were purified by the caprylic acid precipitation method described by Russo, et al., *Anal. Biochem.* (1983) 65:269-271. Paragon analysis of the immunoglobulins and double-diffusion Ouchterlony analysis showed that all the immunoglobulins were of the type IgM.

D. -ELISA Assay for Platelet Factor 4

Platelet factor 4 was diluted in 0.1 M acetic acid and 10 ng/well was pipetted into a 96-well Dynatech Immulon plate. The solution was dried down at room temperature overnight. The plate was blocked by incubation of the wells with 2.5% FCS in PBS. Hybridoma medium, immunoglobulin or antiserum was then added at an appropriate dilution. The plates were then incubated at 37° C. for two hours and washed three times with 3.5% FCS in PBS. Vector Labs avidin-biotin horseradish peroxidase (HRP) ELISA reagents were used according to the manufacturer's directions. The wells were washed with 2.5% FCS in PBS between each step. The positive wells were visualized by the addition of 0.4 mg/ml o-phenylenediamine in 0.1 M sodium citrate solution containing four bacterial LPS of 30% hydrogen peroxide/10 ml of solution. The reaction was allowed to continue for 30 min at room temperature. The reaction was stopped by the addition of 50 bacterial LPS 1.4 N $H_2SO_4$/well.

E. Production of Polyclonal Anti-Platelet Factor 4 Antiserum

Balb/C mice were immunized with nitrocellulose immobilized platelet factor 4. The purpose of this immunization protocol is to avoid rapid clearance of the polypeptide by the host. In this way, immunization can be effected by very small amounts of platelet factor 4.

A solution of platelet factor 4 in 0.1 M acetic acid was dotted onto small pieces of nitrocellulose (Schleicher & Schuell, 0.45 μm) and allowed to dry. The pieces of nitrocellulose were placed into the peritoneal cavity of 3 Balb/C mice for the primary immunization (0.375 ng/mouse). The mice were also given an intraperitoneal injection of 0.1 ml complete Freund's adjuvant. The mice were boosted twice at 2-week intervals with platelet factor 4 immobilized on nitrocellulose. For boosting, the nitrocellulose was cut up, homogenized with 0.1 ml water and 0.1 ml incomplete Freund's adjuvant and injected subcutaneously (0.125 ng/mouse). The mouse sera were tested for specificity against platelet factor 4 by the ELISA assay previously described, with HRP conjugated protein A used as the second step reagent. The sera were tested against platelet factor 4 peptide-KLH conjugate and a blocked plate to show specificity.

EXAMPLE 5

Preparation of Synthetic Platelet Factor 4 Oligonucleotides

A. Synthesis of Platelet Factor 4 Gene

Synthetic platelet factor 4 genes were designed which use bacterial codons optimized for high levels of expression. In addition, the sequence is designed for usage in *E. coli* and a number of restriction enzyme recognition sites were devised to allow for ease of modification of the coding sequence. When possible, the new restriction sites left the amino acid sequence of the gene unaltered, however in some cases incorporation of the new restriction site yielded an altered amino acid sequence.

Single stranded overlapping sequences were prepared, combined in an annealing medium and ligated to provide the complete gene with appropriate termini for insertion into an expression vector in reading phase to prepare a fused protein from which platelet factor 4 could be isolated. The single stranded segments were 5'-phosphorylated with T4 polynucleotide ligase and annealed by combining 200 pM of each segment in a 30 μl reaction volume (30 mM ATP, 10 mM DTT, 10 mM $MgCl_2$ 1 μg/ml spermidine, 100 mM Tris-HCl, pH 7.8 and T4 DNA ligase. The dsDNA was digested with BssHII and BamHI and purified on a 7% native polyacrylamide gel.

The following sequence was prepared:

B. Description of Cloning and Expression Plasmids

1. Plasmid plac/cro-β gal. The controlling elements of the vector plac/cro-β gal consist of the operator-promoter region of *E. coli* lactose (lac) operon, as well as the ribosome-binding sites of lac and cro. This vector is derived from plasmids pTR213 (Roberts et al., *Proc. Natl. Acad. Sci. USA* (1978) 76:760) and PLG300 (Guarente et al., *Cell* (1980) 20:543)

Plasmid plac/cro-β gal was constructed by ligating a 0.96 kb PstI-BglII fragment from pTR213 and a 5.54 kb PstI-BamHI fragment from pLG300 in the presence of the oligonucleotide linker which had been digested with BamHI and BglII:

AAAGATCTCAGGCCTCGAGGATCC
TTTCTAGAGTCCGGATCTCCTAGG

This linker served the following purposes: (1) to regenerate the BglII and BamHI sites from the parental plasmids, (2) to provide additional sites for the insertion of foreign DNA, and, (3) to allow the inserted DNA to be in the correct translational reading frames with respect to the cro 5'-gal coding sequence. 2. Plasmid ptac/cro-β gal. Expression vector ptac/cro-β gal is similar to plac/cro-β gal, with the exception that the promoter of ptac/cro-β gal consists of the −35 region from the promoter of the tryptophan operon and the Pribnow box (−10 region) of the lac operon. This hybrid promoter allows a higher level of expression than plac/cro-β gal. Plasmid ptac/cro-β gal is derived from plasmid pDR540 (Russell and Bennett, Gene (1983) 20:231) and plac/cro-β gal.

Plasmid ptac/cro-β gal was constructed in two steps. First, a 0.87 kb RsaI fragment of plac/cro-β gal plasmid was inserted into pDR540 at the BamHI site, which was previously converted to blunt ends by the action of the Klenow fragment of DNA polymerase I. The orientation of the inserted DNA was such that the ribosome binding site and the coding sequence of cro were located downstream from the ribosome binding site of lac. The resulting plasmid, ptac/cro, contained both ribosome binding sites of lac and cro, and the N-terminal coding sequences of cro. The second step in the construction of ptac/cro-β gal was achieved by ligating the 1.16 kb and the 5.54 kb PstI-BamHI fragments from ptac/cro and pLG300 plasmids, respectively. The structure of ptac/cro-β gal was therefore similar to plac/cro-β gal, with the exception of the hybrid promoter region; the plasmid is referred to as pSM1,2/Tac. 3. Plasmed pBM11, described in copending U.S. application Ser. No. 115,139 by Liu et al., allows cloning of a foreign gene downstream of the DNA sequences coding for the 33 N-terminal amino acids of the bacteriophage λ N-gene at a BamHI restriction site. Upon induction of the λ PL promoter by inactivation of the C1857 temperature-sensitive repressor at 42° C., the foreign gene product is expressed as the C-terminal part of a fusion protein whose N-terminal sequence is that of the N-gene. 4. Plasmed pBM11JM4, described in copending U.S. application Ser. No. 115,139 by Liu et al., is derived from pBM11 and allows a foreign gene to be cloned at a BamHI restriction site directly after the initiating methionine of the N-gene. 5. Plasmed pBM11/NDP, described in copending U.S. application Ser. No. 115,139 by Liu et al., is derived from pBM11 and has DNA sequences coding for an acid labile aspartic acid-proline dipeptide inserted between the sequences coding for the N-gene and the foreign gene.

6. Plasmed pBM11/PAD, described in copending U.S. application Ser. No. 115,139 by Liu et al., is derived from plasmid pBM11M4 and allows a foreign gene to be cloned at a HindIII, SmaI or BamHI downstream from a modified alkaline phosphatase signal sequence. 7. Linearized ptrpED5-1. The plasmid ptrpED5-1 (Hallewell and Entage, Gene (1980) 9:27; Tacon et al., Mol. Gen. Genet. (1980) 177:427) is digested with endonucleases BssHII and BamHI and a substantially full length fragment lacking the trp D gene and having a truncated trp E gene is isolated by preparative gel electrophoresis.

Figure 1:
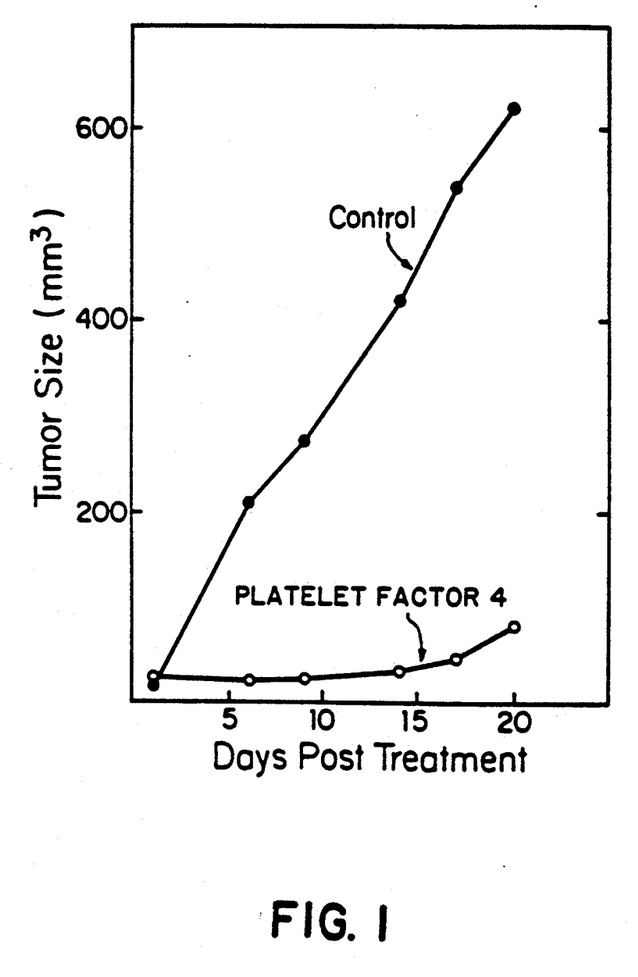
FIG. 1 is a chart comparing the effect of platelet factor 4 on the growth of a tumor in athymic mice.
Figure 2:
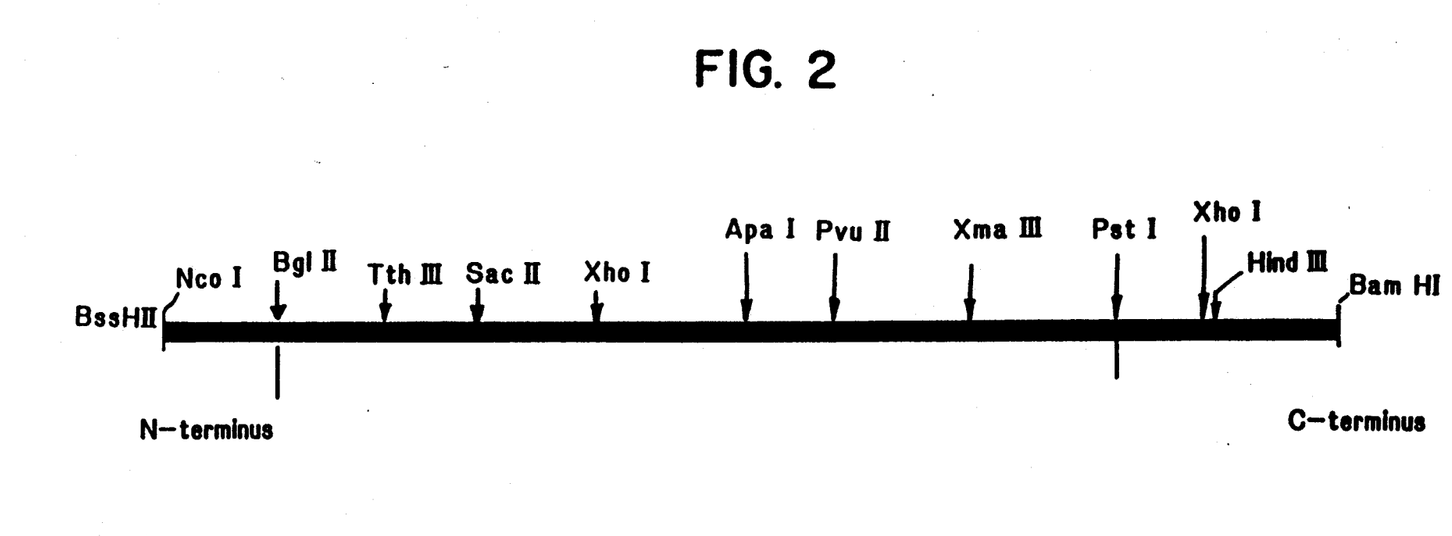
FIG. 2 is a restriction map of the platelet factor 4 synthetic gene.
Figure 3:
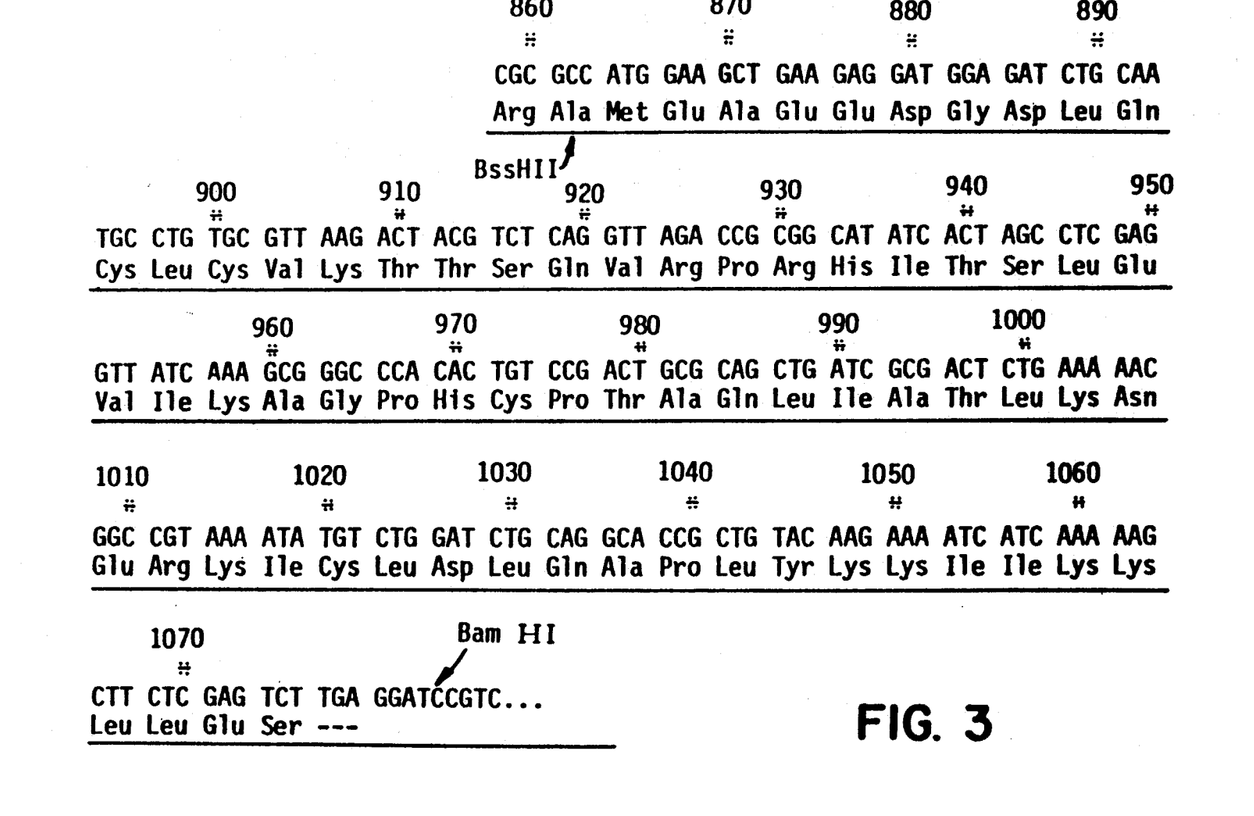
FIG. 3 is the DNA sequence of platelet factor 4 indicating the predicted amino acids.

C. Preparation of Recombinant Platelet Factor 4 Genes 1. Construction of pTac/Cro/PF4. A synthetic gene was cloned in a suitable E. coli cloning plasmid to provide plasmid pHC PF4. A restriction map (FIG. 2) and nucleotide sequence (FIG. 3) are shown in the figures. pHC PF4 was cleaved with BssHII, at the 5' end of the arg codon, filled in with the Klenow fragment, cleaved with BamHI and the PF4 encoding fragment was purified by agarose gel electrophoresis. The fragment was inserted into pSM1,2/Tac, which had been cleaved with StuI and BamHI with the polylinker providing coding for K-D-L-R, and the resulting plasmid ptac/ PF4 used to transform E. coli NF1829. The coding sequence had 21 codons of the cro 5'-terminus 4 codons from the linker and began with the arg codon of PF4. Colonies harboring the correct plasmids were identified by restriction digestion of mini-prep DNA.

2. Preparation of ptrpED5-1/PF4. The platelet factor 4 gene is ligated to the linearized ptrpED5-1 plasmid to provide plasmed ptrp/ PF4 and the ligation mixture is used to transform E. coli HB101 cells. Transformants are selected by ampicillin resistance and the plasmids analyzed by restriction endouclease digestion.

3. Preparation of pBMl1/PF4 (authentic Platelet Factor 4). The nucleotide sequence and corresponding amino acid sequence of the synthetic platelet factor 4 gene expressed as an authentic protein downstream of an initiating methionine in the expression vector pBM11 is as follows.

```
PF4 →
 M    E    A    E    E    D    G    D    L    Q    C    L    C    V
ATG  GAA  GCT  GAA  GAG  GAT  GGA  GAT  CTG  CAA  TGC  CTG  TGC  GTT

K    T    T    S    Q    V    R    P    R    H    I    T    S    L
AAG  ACT  ACG  TCT  CAG  GTT  AGA  CCG  CGG  CAT  ATC  ACT  AGC  CTC

E    V    I    K    A    G    P    H    C    P    T    A    Q    L
GAG  GTT  ATC  AAA  GCG  GGC  CCA  CAC  TGT  CCG  ACT  GCG  CAG  CTG

I    A    T    L    K    N    G    R    K    I    C    L    D    L
ATC  GCG  ACT  CTG  AAA  AAC  GGC  CGT  AAA  ATA  TGT  CTG  GAT  CTG

Q    A    P    L    Y    K    K    I    I    K    K    L    L    E
CAG  GCA  CCG  CTG  TAC  AAG  AAA  ATC  ATC  AAA  AAG  CTT  CTC  GAG

S   ***
TCT  TGA
```

4. Preparation of pBM11/N/PF4 (N-gene/Platelet Factor 4). The nucleotide sequence and corresponding amino acid sequence of the synthetic platelet factor 4 gene in fusion downstream of the nucleotide sequences coding for the first 33 amino acids of the bacterio-phage Asp-Pro (***) in the expression vector pBM11 is as follows.

```
N-gene →
 M    D    A    Q    T    R    R    R    E    R    R    A    E    K
ATG  GAT  GCA  CAA  ACA  CGC  CGC  CGC  GAA  CGT  CGC  GCA  GAG  AAA Q    A    Q    W    K    A    A    N    P    L    L    V    G    V
CAG  GCT  CAA  TGG  AAA  GCA  GCA  AAT  CCC  CTG  TTG  GTT  GGG  GTA

***  ***       PF4 →
 S    A    K    P    V    R    I    D    P    M    E    A    E    E
AGC  GCA  AAA  CCA  GTT  CGG  ATC  GAT  CCC  ATG  GAA  GCT  GAA  GAG

D    G    D    L    Q    C    L    C    V    K    T    T    S    Q
GAT  GGA  GAT  CTG  CAA  TGC  CTG  TGC  GTT  AAG  ACT  ACG  TCT  CAG

V    R    P    R    H    I    T    S    L    E    V    I    K    A
GTT  AGA  CCG  CGG  CAT  ATC  ACT  AGC  CTC  GAG  GTT  ATC  AAA  GCG

G    P    H    C    P    T    A    Q    L    I    A    T    L    K
GGC  CCA  CAC  TGT  CCG  ACT  GCG  CAG  CTG  ATC  GCG  ACT  CTG  AAA

N    G    R    K    I    C    L    D    L    Q    A    P    L    Y
AAC  GGC  CGT  AAA  ATA  TGT  CTG  GAT  CTG  CAG  GCA  CCG  CTG  TAC

K    K    I    I    K    K    L    L    E    S    ***
AAG  AAA  ATC  ATC  AAA  AAG  CTT  CTC  GAG  TCT  TGA
```

λ N-gene in the expression vector pBM11 is as follows.

6. Preparation of pBM11/PAD/PF4 (Signal sequence of alkaline phosphatase with Asp as residue 2

```
N-gene →
 M    D    A    Q    T    R    R    R    E    R    R    A    E    K
ATG  GAT  GCA  CAA  ACA  CGC  CGC  CGC  GAA  CGT  CGC  GCA  GAG  AAA Q    A    Q    W    K    A    A    N    P    L    L    V    G    V
CAG  GCT  CAA  TGG  AAA  GCA  GCA  AAT  CCC  CTG  TTG  GTT  GGG  GTA PF4 →
 S    A    K    P    V    R    I    R    M    E    A    E    E    D
AGC  GCA  AAA  CCA  GTT  CGG  ATC  CGC  ATG  GAA  GCT  GAA  GAG  GAT G    D    L    Q    C    L    C    V    K    T    T    S    Q    V
GGA  GAT  CTG  CAA  TGC  CTG  TGC  GTT  AAG  ACT  ACG  TCT  CAG  GTT R    P    R    H    I    T    S    L    E    V    I    K    A    G
AGA  CCG  CGG  CAT  ATC  ACT  AGC  CTC  GAG  GTT  ATC  AAA  GCG  GGC P    H    C    P    T    A    Q    L    I    A    T    L    K    N
CCA  CAC  TGT  CCG  ACT  GCG  CAG  CTG  ATC  GCG  ACT  CTG  AAA  AAC G    R    K    I    C    L    D    L    Q    A    P    L    Y    K
GGC  CGT  AAA  ATA  TGT  CTG  GAT  CTG  CAG  GCA  CCG  CTG  TAC  AAG K    I    I    K    K    L    L    E    S    ***
AAA  ATC  ATC  AAA  AAG  CTT  CTC  GAG  TCT  TGA
```

5. Preparation of pBM11/NDP/PF4 (N-gene/DP/-Platelet Factor 4). The nucleotide sequence and corresponding amino acid sequence of the synthetic platelet factor 4 gene in fusion downstream of the nucleotide sequences coding for the first 32 amino acids of the bacteriophage λ N-gene and the acid labile dipeptide instead of Lys/Platelet Factor 4). The nucleotide sequence and corresponding amino acid sequence of the synthetic platelet factor 4 gene in fusion downstream of the nucleotide sequences coding for a modified alkaline phosphatase signal peptide is as follows. Predicted cleavage site is noted with (***).

```
Signal sequence →
 M    D    Q    S    T    I    A    L    A    L    L    P    L    L
ATG  GAT  CAA  TCT  ACA  ATC  GCC  CTC  GCA  CTT  CTC  CCA  CTG  CTG

***  PF4 →
 F    T    P    V    T    K    A    E    A    E    E    D    G    D
TTC  ACT  CCA  GTG  ACA  AAA  GCT  GAA  GCT  GAA  GAG  GAT  GGA  GAT

L    Q    C    L    C    V    K    T    T    S    Q    V    R    P
CTG  CAA  TGC  CTG  TGC  GTT  AAG  ACT  ACG  TCT  CAG  GTT  AGA  CCG

R    H    I    T    S    L    E    V    I    K    A    G    P    H
CGG  CAT  ATC  ACT  AGC  CTC  GAG  GTT  ATC  AAA  GCG  GGC  CCA  CAC
```

| C | P | T | A | Q | L | I | A | T | L | K | N | G | R |
|---|---|---|---|---|---|---|---|---|---|---|---|---|---|
| TGT | CCG | ACT | GCG | CAG | CTG | ATC | GCG | ACT | CTG | AAA | AAC | GGC | CGT |

| K | I | C | L | D | L | Q | A | P | L | Y | K | K | I |
|---|---|---|---|---|---|---|---|---|---|---|---|---|---|
| AAA | ATA | TGT | CTG | GAT | CTG | CAG | GCA | CCG | CTG | TAC | AAG | AAA | ATC |

| I | K | K | L | L | E | S | *** |
|---|---|---|---|---|---|---|---|
| ATC | AAA | AAG | CTT | CTC | GAG | TCT | TGA |

EXAMPLE 6

Preparation of Recombinant Platelet Factor 4

A. Isolation of PF4 Expressed in Recombinant Bacteria

1. *E. coli* NF1829 transformants containing the pTac/PF4 plasmids were grown overnight with or without 1% lactose, spun, boiled for 10 min in 1X Laemmli SDS-PAGE sample buffer and analyzed by electrophoresis on 17.5% polyacrylamide-SDS gels. For large scale preparations, single colonies were grown in 2 ml of L-broth for 8 hr and transferred to 1 L of L-broth containing 1% lactose plus antibiotics and grown overnight at 37° C. The recombinant platelet factor 4 having 21 codons of the cro gene was purified as follows: one L of the bacteria induced with 1% lactose was grown, followed by centrifugation to form a pellet and the pellet frozen at −70° C. After resuspending the pellet in 50 ml 50 mM Tris, pH 7.9, 0.2 M NaCl, 2 mM EDTA, and 2 mM 2-mercaptoethanol, lysozyme was added to 200 μg/ml and the mixture incubated for 20-30 min on ice while shaking. To the mixture was added Triton X-100 to 1% and the mixture incubated for 10-20 min on ice while shaking, followed by the addition of Zwittergent (Calbiochem) to 0.5% following by incubation for 10-20 min on ice while shaking. The mixture was sonicated on ice with a 0.25 inch probe for 2-3 min while pulsing to provide a mixture which could be pipetted. The mixture was then loaded onto 10 ml 40% sucrose in STE, spun at 13,000 for 30 min at 5° C. in a SW28 rotor and the supernatants removed. The pellet was resuspended in 5-10 ml of 0.01 M of Tris, pH 7.2, 0.15 M NaCl and the sample analyzed by SDS-PAGE (17.5%). The gel was developed by Coomassie blue staining demonstrating that the fusion protein was produced in *E. coli*.

2. The transformants are grown at 37° C. to about $10^8$ cells/ml in Luria broth and 3-indolylacetic acid (IAA) is added to about 1 mM and growth continued for about 1 hr. Aliquots (1 ml) are centrifuged for a few seconds in an Eppendorf centrifuge and the pellets are suspended in 500 μl of 7% formic acid containing 5 mg/ml cyanogen bromide. After 24 hr at room temperature, aliquots are diluted tenfold in water and the diluted samples assayed for platelet factor 4. Since platelet factor 4 has no internal methionine, having an N-terminal methionine cleavage of the fused protein provides platelet factor 4 having the same amino acid sequence as naturally occurring platelet factor 4.

TABLE III

| Expression of PF4 in Different Bacterial Expression Systems | |
|---|---|
| | Percent of Total Protein |
| pTac/Cro/PF4 | 5% |
| pBM11/Ngene/PF4 | 20% |
| pBM11/Ngene/DP/PF4 | 20% |
| pBM11/PAD/PF4 | 15% |

TABLE III-continued

| Expression of PF4 in Different Bacterial Expression Systems | |
|---|---|
| | Percent of Total Protein |
| pBM11/PF4 | 2% |

EXAMPLE 7

Biological Activity of Platelet Factor 4 Prepared in Procaryotic Cells

A. Inhibition of DNA Synthesis

The highest activity seen was with the fusion protein from the plasmed pBM11/Ngene/PF4 (see Example 1A). Fifty percent of maximum inhibition of A549 cells was obtained with 0.67 μg/well.

B. Inhibition of Growth of Tumors in Nude Mice

Male nude mice were injected with platelet factor 4 or phosphate buffered saline at 2- to 3-day intervals, as described in Example 1C. As shown in Table IV, platelet factor 4 significantly inhibited tumor growth.

TABLE IV

| Effect of Recombinant Platelet Factor 4 on Growth of Tumors in Nude Mice | | |
|---|---|---|
| | Tumor size (mm³) | |
| Days Post Treatment | Control | Platelet Factor 4 |
| 0 | 17 | 25 |
| 6 | 205 | 25 |
| 9 | 275 | 25 |
| 14 | 420 | 40 |
| 17 | 545 | 50 |
| 20 | 635 | 85 |

It is evident from the above results that the subject compounds find a wide variety of applications. Particularly, the compounds can be used in the diagnosis and treatment of neoplastic states. In therapy, the compounds can provide for the slowing of tumor cell growth, so as to be used jointly with other modes of treatment for the destruction of tumor cells. For diagnosis, the subject compounds are found to induce the production of p52, so that upon administration of the subject compounds to a host, enhanced levels of p52 would be indicative of the presence of tumor cells. This can be very important during the treatment of a neoplastic state to determine whether the removal of the tumor cells has been successful or metastases have occurred. The subject compounds can also be used as reagents in diagnostic assays for the presence of platelet factor 4 or platelet factor 4 receptors.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for inhibiting proliferation of a plurality of neoplastic cells, said method comprising administering to an individual a proliferation inhibiting amount of platelet factor 4 having the amino acid sequence of;

E-A-E-E-D-G-D-L-Q-C-L-C-V-K-T-T-S-Q-V-R-P-R-H-I-T-S-L-E-V-I-K-A-G-P-H-C-P-T-A-Q-L-I-A-T-L-K-N-G-R-K-I-C-L-D-L-Q-A-P-L-Y-K-K-I-I-K-K-L-L-E-S.

2. A method of inhibiting the growth of neoplastic cells comprising administering to an individual platelet factor 4 in an amount effective at inhibiting cell growth, wherein the platelet factor 4 is characterized as:

(a) having a molecular weight of about 7,000 daltons;

(b) being isolable from platelets by extraction with approximately 0.3 M ethanolic hydrochloric acid, precipitation with cold ethanol, ether and dialysis against 0.1–0.5 M acetic acid, and gel permeation chromatography employing Biogel P-10 and 1 M acetic acid eluant;

(c) having the amino-terminal amino acid sequence E-A-E-E-D; and (d) being capable of inhibiting tumor cell growth in the colony inhibition test.

* * * * *